United States Patent
Panteleeva et al.

(10) Patent No.: US 10,473,568 B2
(45) Date of Patent: Nov. 12, 2019

(54) SUPPORT FOR SAMPLE TUBES FOR THE SONICATION OF A BIOLOGICAL MATERIAL

(71) Applicant: Diagenode S.A., Seraing (BE)

(72) Inventors: Irina Panteleeva, Seraing (BE); Gilles Ansay, Seraing (BE); Jerome Kroonen, Liège (BE)

(73) Assignee: Diagenode S.A., Seraing (BE)

( * ) Notice: Subject to any disclaimer, the term of this patent is extended or adjusted under 35 U.S.C. 154(b) by 0 days.

(21) Appl. No.: 15/786,930

(22) Filed: Oct. 18, 2017

(65) Prior Publication Data
US 2018/0106705 A1     Apr. 19, 2018

(30) Foreign Application Priority Data
Oct. 18, 2016   (BE) .................................. 2016/5781

(51) Int. Cl.
*G01N 1/40* (2006.01)
*B01L 9/06* (2006.01)
(Continued)

(52) U.S. Cl.
CPC ........ *G01N 1/4077* (2013.01); *B01L 3/50273* (2013.01); *B01L 9/06* (2013.01); *B01L 9/523* (2013.01); *C12N 15/1003* (2013.01); *C12Q 1/6806* (2013.01); *B01L 2400/0439* (2013.01); *B06B 2201/77* (2013.01); *G01N 2001/4094* (2013.01)

(58) Field of Classification Search
CPC . C12Q 1/6806; G01N 1/4077; C12N 15/1003
See application file for complete search history.

(56) References Cited

U.S. PATENT DOCUMENTS 4,874,137 A     10/1989  Chiba
6,318,158 B1 *  11/2001  Breen ................. B01F 11/0266
                                                        422/128
(Continued)

FOREIGN PATENT DOCUMENTS

EP     2511380 A1    10/2012
GB     1363934 A      8/1974

OTHER PUBLICATIONS

Sep. 1, 2015, "Bioruptor® Pico Sonication System", user manual, Diagenode Innovating Epigenetics Solutions.
(Continued)

*Primary Examiner* — Narayan K Bhat
(74) *Attorney, Agent, or Firm* — Kolitch Romano LLP (57) ABSTRACT

Assembly kit, comprising a sonication device (10) and a support (20) for sample tubes (30). The device comprises a tank (13) and an ultrasound wave generator (15) coupled to the tank and designed to generate ultrasound waves having a frequency of between 20 kHz and 80 kHz. The tank comprises an indicator (132) of a level (133) of liquid. The support for sample tubes comprises a means (21) for the support of several sample tubes of a size of 0.2 ml, a rod (22) secured to the support means, and a means (23) for suspending the rod in the tank. The rod has a length such that, in the assembly position, the sample tubes (30) are positioned with their lower end between 8 mm and 12 mm below the indicator (132) of the level of liquid.

12 Claims, 6 Drawing Sheets

(51) Int. Cl.
 *C12Q 1/6806* (2018.01)
 *B01L 3/00* (2006.01)
 *B01L 9/00* (2006.01)
 *C12N 15/10* (2006.01)

(56) References Cited

U.S. PATENT DOCUMENTS

2002/0009015 A1* 1/2002 Laugharn, Jr. .......... B01F 11/02
 366/108
2012/0264228 A1* 10/2012 Poncelet .............. C12Q 1/6806
 436/174

OTHER PUBLICATIONS

Mar. 2, 2017, Search Report from the European Patent Office, in Belgian Application No. 201605781, which is the priority application to this U.S. application.

* cited by examiner

SUPPORT FOR SAMPLE TUBES FOR THE SONICATION OF A BIOLOGICAL MATERIAL

CROSS-REFERENCE TO RELATED APPLICATION

This application claims priority to Belgian Patent Application No. 2016/5781, filed Oct. 18, 2016, which is hereby incorporated by reference.

BRIEF SUMMARY OF THE INVENTION

The present invention relates to devices, supports and processes for the fragmentation of a biological material, in particular DNA. In particular, the present invention relates to devices and processes for the fragmentation of said biological material by shearing by means of ultrasound waves, also referred to as sonication.

The use of ultrasound to create a focused mechanical stress in order to rupture cell walls has been known for a long time, for example from GB 1363934 and U.S. Pat. No. 4,874,137. The ultrasound waves pass through the sample, expanding and contracting the liquid. During the expansion, the molecules are moved apart from one another and cavities or bubbles are formed during a process referred to as cavitation. The bubble continues to absorb energy until it can no longer remain stable and then implodes, producing intense focused shearing forces which rupture the cell walls.

It is known that indirect excitation of said biological material by ultrasound waves, generated at a remote location and caused to propagate through one or more media before arriving at the material to be fragmented, gives better results. The indirect excitation is alleged to cause a gentler excitation, such that more uniform fragments are obtained.

The use of ultrasound waves of frequency between 20 kHz and 40 kHz to fragment DNA and RNA sequences is also known from the document EP 2511380, of 17 Oct. 2012, in the name of the applicant. The use of a frequency of between 28 kHz and 80 kHz makes it possible to obtain smaller size distributions for the fragments obtained, to reduce the time necessary to obtain such fragments, and to use lower ultrasound energy intensities for shearing, compared with a lower frequency, in particular 20 kHz.

Several apparatus suitable for the fragmentation of DNA by ultrasound are sold by the applicant under the names Bioruptor® Plus and Bioruptor® Pico (Diagenode, Belgium). DNA or chromatin samples are suspended in a liquid solution in a sample tube. The sample tube is suspended in a tank filled with a liquid medium (generally water). Ultrasound wave transducers are coupled to the lower wall of the tank. When the transducers are activated, ultrasound waves having a frequency of between 20 kHz and 60 kHz are generated at the lower wall of the tank and propagate through the liquid medium toward the sample tube. From the sample tube, the ultrasound waves are transmitted to the contents thereof, which then undergoes mechanical stresses as indicated above.

The sample tubes of use in the abovementioned apparatus have a size which can vary between 0.1 ml and 50 ml. In DNA fragmentation, there is a tendency to fragment samples of a smaller volume. A preferred volume of DNA solution subjected to ultrasound waves is 50 µl. For this volume, sample tubes of a size of 0.2 ml, also referred to as "microtubes", are preferably used.

It has been observed that the results obtained with this type of sample tube are highly random. Consequently, the aim of the present invention is to provide devices and processes which make it possible to avoid the abovementioned drawbacks. In particular, one aim of the invention is to provide devices, or even assembly kits, and processes which make it possible to fragment a biological material in sample tubes of a size of 0.2 ml, such that fragments having a small variance/a small standard deviation in terms of size are obtained.

Another aim of the invention is to provide devices, or even assembly kits, and processes which make it possible to reduce the time needed to fragment the DNA and to increase the throughput using sample tubes of a size of 0.2 ml.

According to a first aspect, the invention relates to an assembly kit as detailed in the appended claims. The assembly kit according to the invention comprises a sonication device, a support for sample tubes, and optionally several sample tubes of a size of 0.2 ml. The sonication device comprises a tank and at least one ultrasound wave generator coupled to an outer face of the tank. This ultrasound wave generator is advantageously designed to generate ultrasound waves having a frequency of between 20 kHz and 80 kHz. The tank comprises an indicator of the level of liquid in the tank. The support for sample tubes comprises a means for the support of several sample tubes of a size of 0.2 ml, a rod having a lower end and an upper end, and a means for suspending the rod in the tank. The rod is secured to the support means at its lower end.

According to the present aspect, the rod has a length such that, in the assembly position, the sample tubes introduced into the support means are positioned with their lower end between 8 mm and 12 mm below the indicator of the level of liquid, preferably between 9 mm and 11.5 mm, preferably between 9.5 mm and 11 mm.

Surprisingly, it has been observed that positioning the sample tubes at the abovementioned depth makes it possible to obtain an extraordinarily more effective fragmentation, and therefore to reduce the sonication time for this type of sample tube, and consequently to increase the throughput of assembly kits of the abovementioned type. With a reduced sonication time, it is possible to obtain a very narrow fragment size distribution, which facilitates use in subsequent applications.

According to a second aspect, the invention relates to a support for sample tubes of a size of 0.2 ml designed to be used in the assembly kit described above. The support for sample tubes comprises a means for the support of several sample tubes of a size of 0.2 ml, a rod having a lower end and an upper end, and a means for suspending the rod in the tank. The rod is secured to the support means at its lower end.

According to the present aspect, the rod has a length such that, in the assembly position of the support in a tank of a sonication device containing a liquid bath, the sample tubes introduced into the support means are positioned with their lower end between 8 mm and 12 mm below an indicator of the level of liquid, preferably between 9 mm and 11.5 mm, preferably between 9.5 mm and 11 mm.

According to a third aspect, the invention relates to a process for the fragmentation of biological material as detailed in the appended claims.

Additional aspects of the invention are described in the appended dependent claims.

Other features, details and advantages of the invention will emerge from the description and examples given below, nonlimitingly and with reference to the appended drawings.

BRIEF DESCRIPTION OF THE DRAWINGS

FIGS. 9 and 10 each show a graph of the distribution of sizes of DNA sequence fragments as obtained in the comparative examples described below in example 1. The distribution of sizes (in base pairs) is represented graphically relative to fluorescence units (FU). FIG. 9 relates to a sonication with suspension of the samples in the water bath at a depth of 13 mm. FIG. 10 relates to a sonication with suspension of the samples in the water bath at a depth of 7.3 mm.

DETAILED DESCRIPTION OF THE INVENTION

Some aspects of the invention relate to the fragmentation of a biological material. The term "biological material" is intended to mean, for example, within the context of the present invention, DNA, RNA, samples of biological tissues, bacteria, viruses, or animal or plant cells. In particular for the fragmentation of DNA, in the processes according to the invention, use is made, as base material, of genomic or plasmid DNA, or of DNA having a size greater than or equal to 10 000 base pairs (bp).

The fragmentation is carried out by shearing by means of ultrasound waves. According to one aspect of the invention, ultrasound waves having a frequency of greater than or equal to approximately 20 kHz, preferably greater than or equal to approximately 28 kHz, preferably greater than or equal to approximately 36 kHz, and less than or equal to approximately 80 kHz, preferably less than or equal to approximately 60 kHz and preferably less than or equal to approximately 50 kHz, are used. The upper and lower frequency limits indicated may be combined to give optimum frequency ranges.

Such ultrasound waves may be generated by known transducers, such as piezoelectric or magnetostrictive transducers. The excitation of the biological material by the ultrasound waves is indirect, in that the ultrasound waves are generated at a remote location and are caused to propagate through one or several media before arriving at the sequence. The indirect excitation is alleged to cause a gentler excitation, such that more uniform fragments are obtained.

Figure 1:
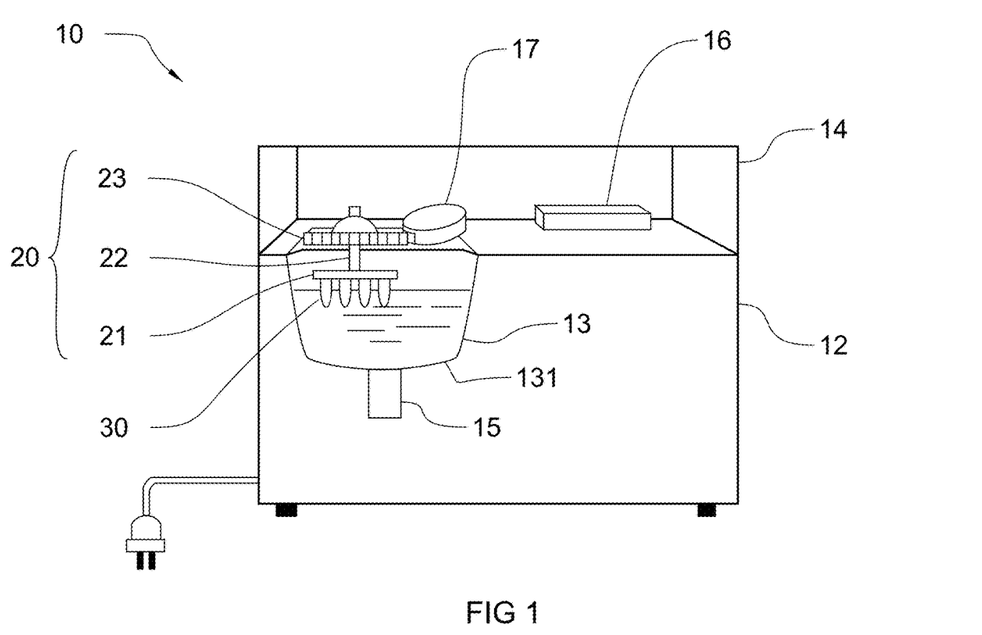
FIG. 1 shows a front view of a sonication device and of a support constituting an assembly kit according to the invention.
Figure 2:
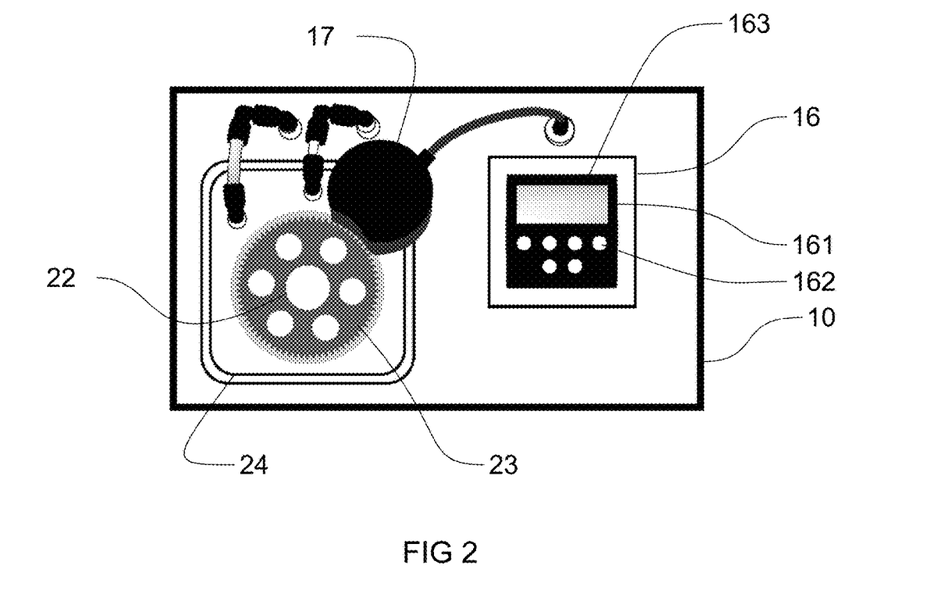
FIG. 2 shows a top view of the device of FIG. 1.

With reference to FIGS. 1 and 2, the invention relates to an assembly kit comprising a device 10, referred to as a sonication device, capable of subjecting a solution of biological material to ultrasound waves in accordance with the various aspects of the present invention. Such a solution may be liquid or of gel type, as is known in the prior art. The sonication device 10 of FIG. 1 is similar, from a construction perspective, to apparatus described in the U.S. Pat. No. 4,874,137, the reference of which is incorporated herein by reference.

The device 10 comprises a main body 12 which contains a tank 13 configured to contain a liquid, preferably distilled water. The device 10 may be closed by a cover 14.

One or more ultrasound wave generators (transducers) 15 are coupled externally to the tank 13, preferably on the outer face of the bottom 131 of the tank 13. The transducers 15 may be of piezoelectric or magnetostrictive type and are configured to generate mechanical vibrations having a frequency as indicated, which are transmitted to the tank 13.

The transducers 15 may be electrically connected to a control and power supply unit 16, which may be configured to control one or more of the following parameters: the excitation frequency, the power, the duration and any other adjustable parameter associated with the generation of the ultrasound waves. The control unit 16 is advantageously provided with a user interface 161, via which one or more of the parameters indicated above may be adjusted. By way of example, the user interface 161 may be provided with one or more control and/or adjustment buttons 162. The parameters may be viewed on a screen 163.

Figure 3:
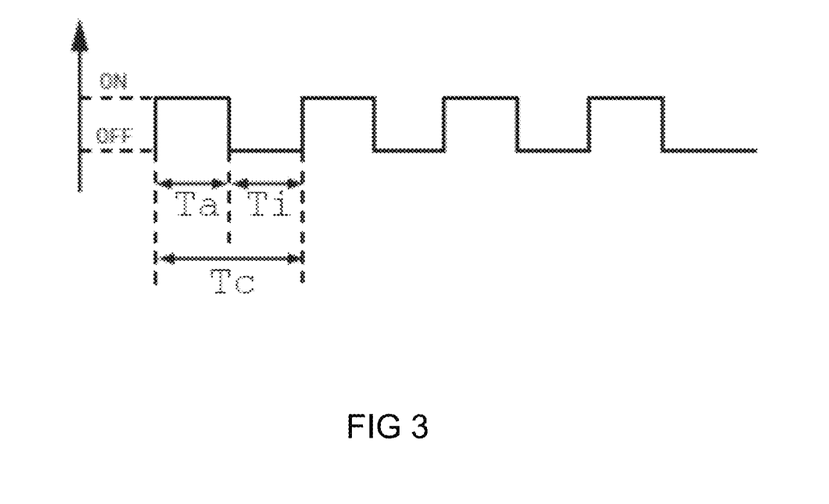
FIG. 3 shows a graph of the intermittent (cyclical) generation of ultrasound waves.

Moreover, the control unit 16 may be configured for an intermittent generation of ultrasound waves. The transducers 15 may be configured to operate intermittently, for example in (equal) cycles formed of an active period (Ta) during which the transducers are active and generate ultrasound waves, and of an inactive period (Ti) during which the transducers are inactive and do not generate ultrasound waves, as illustrated in FIG. 3. The sum of the periods of active and inactive time within a single cycle is referred to as cycle period Tc. The ratio of the active period Ta to the cycle period Tc is referred to as duty ratio. The possible cycle periods fall within the range located between approximately 2 s and approximately 6 minutes (360 s), with cycle periods between approximately 30 s and approximately 3 minutes (180 s) being preferred. Possible duty ratios fall within the range located between approximately 0.1 (10%) and approximately 0.8 (80%), preferably between approximately 0.3 and approximately 0.7.

Figure 4:
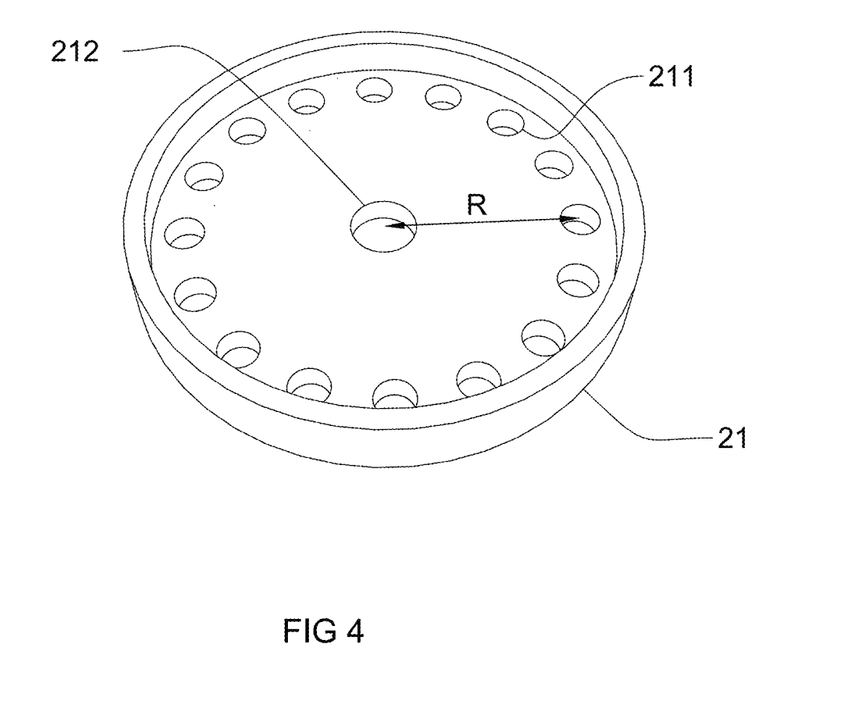
FIG. 4 shows a perspective front view of a support plate for sample tubes according to the various aspects of the invention.

The assembly kit according to the invention further comprises a support 20 for sample tubes, designed to suspend the sample tubes, comprising the solution of biological material to be fragmented, in the tank 13. To this end, the support 20 comprises a plate 21 for supporting several sample tubes, as shown in FIG. 4. The plate 21, which is advantageously circular in shape, comprises several holes 211 arranged advantageously at the periphery of the plate. Advantageously, the holes 211 are uniformly spaced apart and are arranged in a circle such that each hole 211 is positioned at one and the same distance R from the center 212 of the plate 21.

Figure 5:
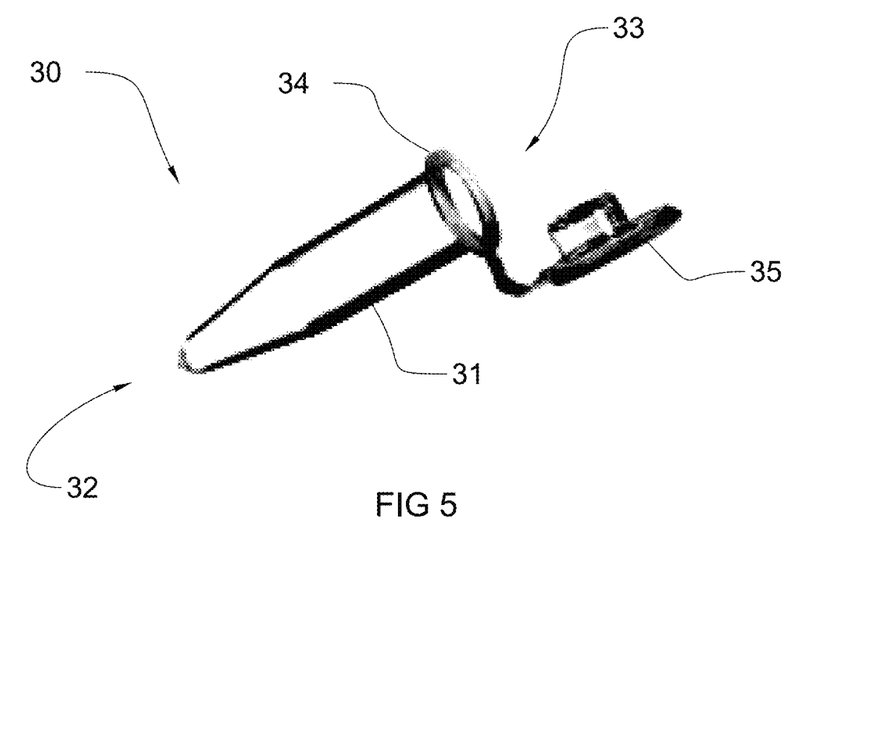
FIG. 5 shows a perspective view of a sample tube (microtube) used in the assembly kits of the invention.

The holes 211 have a diameter enabling the insertion of a sample tube of a predetermined size, in particular of a size of 0.2 ml. With reference to FIG. 5, the sample tube 30 comprises a main body 31 which, in a lower part, is advantageously conical in shape, ending in a point at the lower end 32. The main body 31 comprises an upper part which is advantageously cylindrical in shape. At the upper end 33, the main body 31 ends in a flange 34, protruding relative to the main body, and to which a cap 35 is advantageously attached. The sample tubes 30 are inserted in the holes 211 of the plate 21 such that the main body 31 passes through the holes 211, the flange 34 bearing on the upper face of the plate 21. The sample tubes of a size of 0.2 ml advantageously have a total length (measured from the lower end to the upper end) of between 20.9 mm and 21.8 mm.

Sample tubes made of polypropylene, polymethylpentene or polycarbonate may be used. It has been observed that a sample tube made of polypropylene gives better results, for example the 0.2 ml tubes sold by Diagenode (Belgium), reference C30010020.

A rod 22 is secured via its lower end to the center 212 of the plate 21, for example by screwing. The rod 22 extends upwards relative to the plate 21 until its upper end meets an element 23 located above the tank 13. The rod 22, the plate 21, and consequently the sample tubes 30 inserted into the holes 211 of the plate 21, are suspended in the tank 13 by means of the element 23. This element 23 advantageously takes the form of a gear wheel 23. This gear wheel 23 is supported by a cover 24 which covers the tank 13. The device 10 is advantageously provided with an electric actuator 17 arranged at the cover 24, so as to engage the wheel 23 and cause it to turn about a vertical axis, corresponding advantageously to the axis of the rod 22. This system advantageously makes it possible to cause the support plate 21 to turn at a speed of between 15 rpm and 1 rpm, preferably between 8 rpm and 2 rpm. Alternatively, the support 20 may be suspended in the tank 13 in a fixed position. It should be noted that the support 20 is assembled removably in the tank 13.

Figure 6:
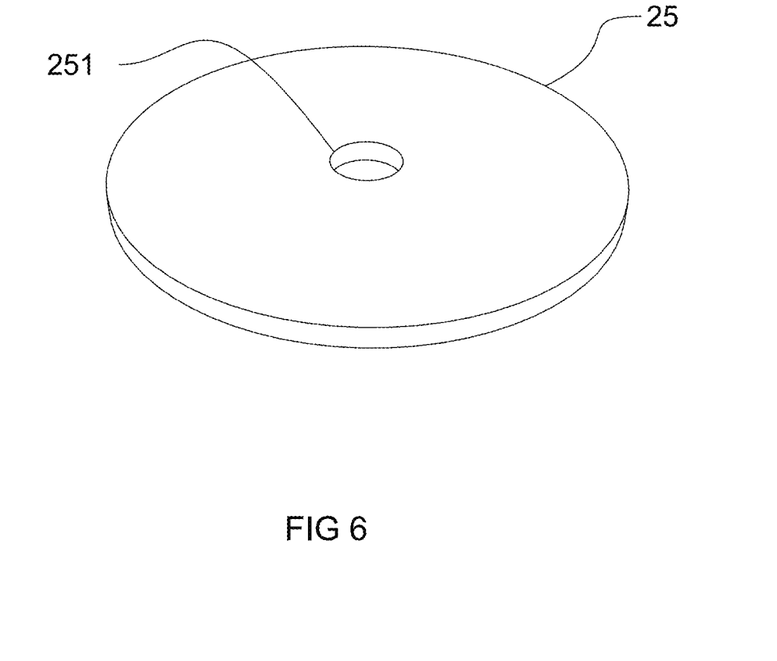
FIG. 6 shows a perspective view of a plate for clamping the sample tubes, which plate is used in the support according to the various aspects of the invention.

With reference to FIG. 6, the support 20 advantageously comprises a plate 25, referred to as a clamping plate, which becomes attached to the plate 21. The clamping plate 25 is attached so as to clamp the upper ends 33 of the sample tubes 30 to the plate 21 and the plate 25. The clamping plate 25 may for example comprise a central hole 251 into which the rod 22 is inserted before screwing the rod to the plate 21. The rod 22 is advantageously provided with a shoulder configured to press the clamping plate 25 against the plate 21.

For the optimum operation of the device 10, the tank 13 must especially be filled with a liquid up to a predetermined level 133. To this end, and with reference to FIG. 7, the tank 13 comprises an indicator 132 of a liquid filling level, advantageously provided on a wall of the tank 13. The sample tubes 30 are suspended by the support 20 so as to be partially submerged in the liquid. The plate 21 for supporting the sample tubes 30 is advantageously placed so as to rest above the liquid level 133.

Figure 7:
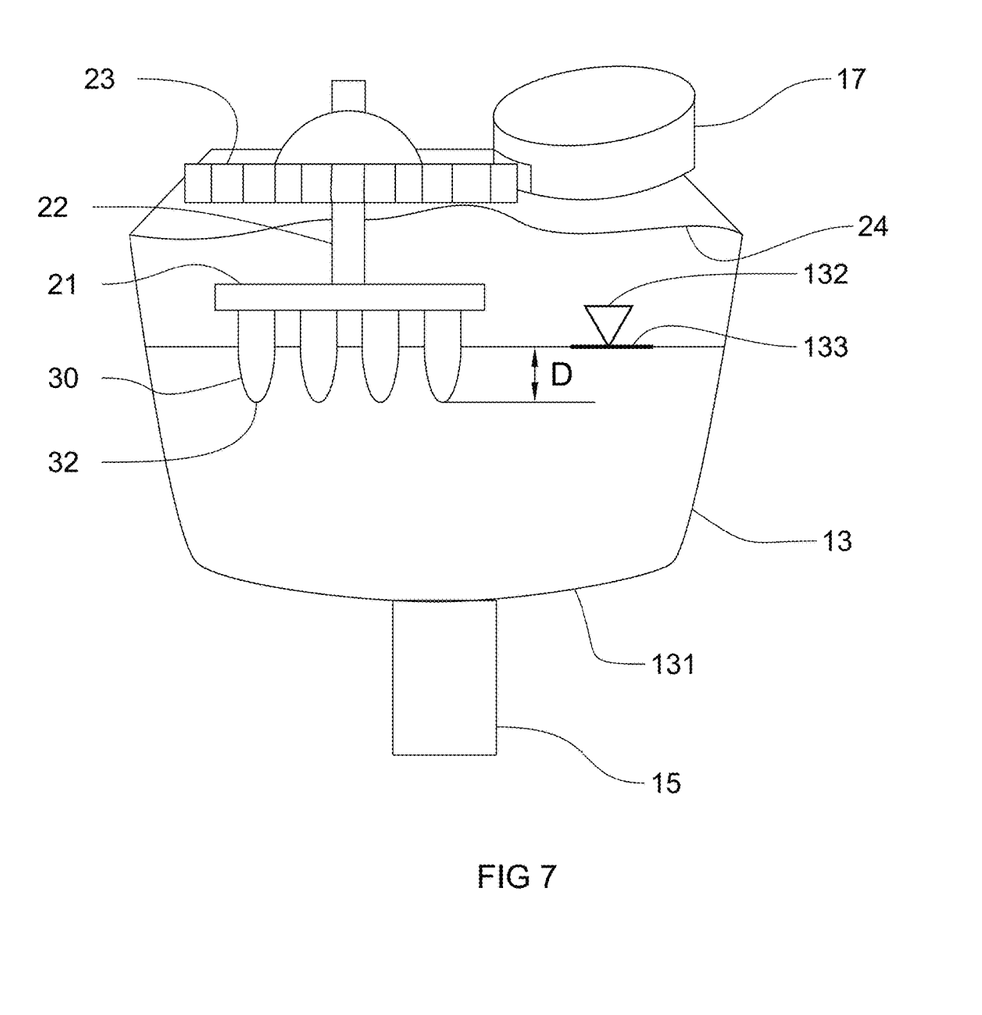
FIG. 7 shows a detail from FIG. 1, showing the way in which the sample tubes are suspended in the tank of a sonication device using the support according to the various aspects of the invention.

Surprisingly, within the context of the present invention, it has been observed that, specifically for sample tubes of a size of 0.2 ml, the vertical positioning of the sample tubes relative to the liquid level 133 is critical for effective fragmentation of the samples. It has been observed that the depth of submersion D of the sample tubes 30 must be in the range between 8 mm and 12 mm, advantageously in the range between 9 mm and 11.5 mm, in order to obtain a significantly more effective fragmentation, making it possible to reduce the sonication time and therefore to increase the throughput in terms of units of samples treated per unit time. As illustrated in the examples described below, this distance is independent of the type of device 10 used and therefore appears to be a general rule applicable to sample tubes of a size of 0.2 ml. In other words, the support 20 must be designed so as to maintain the distance D, between the indicator 132 of the level of liquid in the tank 13 and the lower end of the sample tubes 30, within the abovementioned range. This distance D may be guaranteed by selecting, for example, a suitable length of the rod 22.

The abovementioned distance D is advantageously maintained throughout the entire operation of fragmentation of a sample. This distance D is advantageously fixed.

Advantageously, the number of sample tubes 30 which may be arranged on the plate 21 depends on the distance R of formation of the holes relative to the center 212 of the plate 21. Advantageously, the number of sample tubes 30 to be provided, and therefore the number of holes 211 to be formed on the plate 21, is between 12 and 36. Advantageously, these holes 211 are formed around the circumference of a circle with a radius R of between 25 mm and 50 mm, for example between 30 mm and 45 mm. An optimum ratio between the number of holes 211 and the radius R of the circle on which they are arranged is advantageously less than or equal to 0.7, advantageously less than or equal to 0.67, where R is expressed in mm. The variance of the size of the fragments obtained is significantly reduced when the sample tubes are arranged as described above. The radius R is not restrictive: the constraint for R depends on the size of the tank 13.

For an optimized treatment, the solution should preferably be maintained at a temperature of between 4° C. and 10° C., even during the treatment. Since ultrasound excitation causes an increase in temperature, the device 10 preferably comprises a temperature control unit (cooling unit) configured to maintain the solution at a predetermined temperature. The temperature control unit may be integrated into the device 10, or alternatively may be provided as an external device.

The assembly kits as described above may be used advantageously to carry out the processes of the invention. In order to carry out such processes, the starting biological material is advantageously suitably conditioned. In the particular case of a DNA sequence, this step may comprise a step of extraction and purification of the DNA sequence from a biological sample containing DNA, such as a cell or a tissue.

The process then comprises dissolving the biological material to be fragmented in a sonication solution. In the particular case of a DNA sequence, this step comprises dissolving the DNA sequence obtained in a sonication buffer, such as a TE buffer (Tris-EDTA buffer) having a pH located in the range between approximately 7.5 and approximately 8.0. Other conditioning steps, such as the addition, to the solution containing DNA, of a solid support, of an organic solution, of a detergent, of a positively charged polymer, or of organic molecules, may be advantageous.

The concentration of the biological material in the sonication solution preferably falls within the range located between approximately 0.001 µg/µl (1 ng/µl) and approximately 0.5 µg/µl, preferably between approximately 0.001 µg/µl and approximately 0.25 µg/µl, preferably between approximately 0.001 µg/µl and approximately 0.1 µg/µl. From this solution, a volume of preferably less than or equal to 100 µl, preferably less than or equal to 60 µl, preferably 50 µl, is placed in the sample tube 30.

The sample tube having an isolated volume of sonication solution is then suspended in the liquid bath of the tank 13. To this end, the sample tube 30 is inserted in a hole 211 of the plate 21 which is secured to the rod 22 and suspended in the tank 13 filled with liquid, in particular water, such as distilled water, up to the level 133 indicated by the level indicator 132.

In a following step, the sample tube is subjected to the action of ultrasound waves of a frequency as indicated. One or more protocols may be established for carrying out a shearing/fragmentation treatment according to the invention in order to obtain fragments of the desired (mean) size and having narrow size distributions. Preferably, the processes of the invention make it possible to fragment the biological material into fragments with a size distribution having a coefficient of variance of less than 18%, preferably less than or equal to 15%, preferably less than or equal to 12%, preferably less than or equal to 10%. The protocol may comprise selection of the duration of treatment and/or of the periodicity (intermittent or continuous) of the treatment. The preferred values for the duration and the periodicity are those indicated above. The desired protocol may be programmed into the device 10 by means of the user interface 161.

The device 10 is then started up. The transducer 15 excites the wall of the tank 13. The mechanical vibrations of the tank 13 propagate through the liquid bath in the form of (ultrasonic) pressure waves of the same frequency. The sample tube 30, including the sonication solution, is excited.

Advantageously, the actuator 17 is used to cause the support 20 and the sample tubes 30 to turn about the vertical axis of the rod 22.

EXAMPLE 1

Effect of the Depth of Submersion of the Sample Tubes

Sample preparation: for each test sample, a sample of human genomic DNA (certified initial size of 50 000 bp) was dissolved in a TE buffer (Tris 10 mM, EDTA 1 mM, pH 8.0) to a concentration of 10 ng/µl in order to obtain a sonication solution. Several sonication samples were obtained by placing in each case one volume of 50 µl of the solution into a low-affinity 0.2 ml Diagenode® microtube (catalogue number C30010020). The sample, with the cap closed, was vortexed gently for 10 seconds then centrifuged for 10 seconds to collect the sample at the bottom of the tube before it was subjected to the ultrasound waves.

A total of sixteen (16) of these microtubes were introduced into a support plate as represented in FIG. 4. This plate comprises a total of 16 holes 211 formed 30 mm from the center 212 of the plate. The plate was mounted on a support 20 and introduced into a Bioruptor® Pico sonication device so as to position the microtubes at a depth D (see FIG. 7) of 10.3 mm from the level of the water bath. The support 20 was provided with a gear wheel 23, coupled to an electric motor 17 designed to turn the support plate with the microtubes about a vertical axis (axis of the rod 22) at a rate of 4 rpm.

The sonication frequency was 40 kHz. A sonication of 13 cycles (30 s active period/30 s inactive period) was applied to a bath of distilled water at 4° C. The DNA fragments obtained were analyzed by a Fragment Analyzer™ (Advanced Analytical Technologies, Inc.) and their mean size and coefficient of variance (CV) were calculated.

Figure 8:
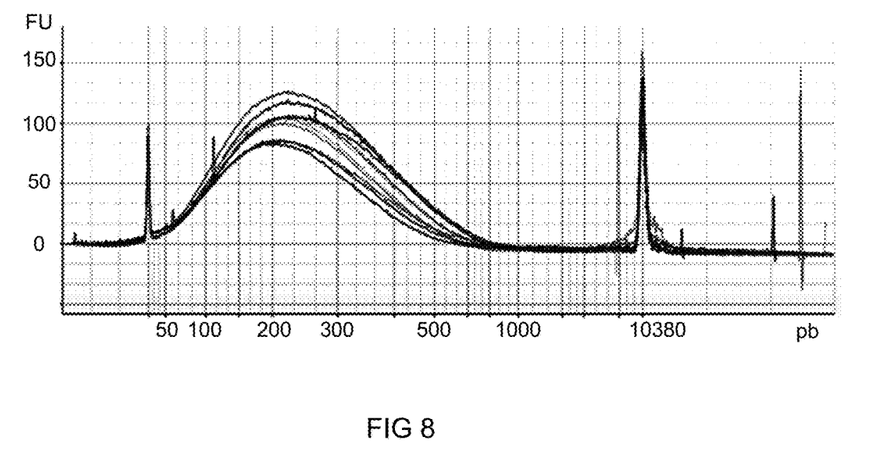
FIG. 8 shows a graph of the distribution of sizes of DNA sequence fragments as obtained in example 1 described below. The distribution of sizes (in base pairs) is represented graphically relative to fluorescence units (FU).

The results are reported in FIG. 8. The mean size of the fragments was 219 bp and the CV was 4.2%.

COMPARATIVE EXAMPLES

The sonication solution of example 1 was used to obtain 32 sonication samples according to the same procedure as for example 1 (0.2 ml microtubes; each with a sample of 50 µl). The support plate of example 1 was used. However, a first rod, shorter than that used for example 1, and a second rod, longer than that used for example 1, were used to suspend the support plate in the tank.

In a first comparative example, 16 microtubes were introduced into the holes of the support plate and suspended in the Bioruptor® Pico so as to position the microtubes at a depth D of 13.0 mm using the second rod for the support.

Figure 9:
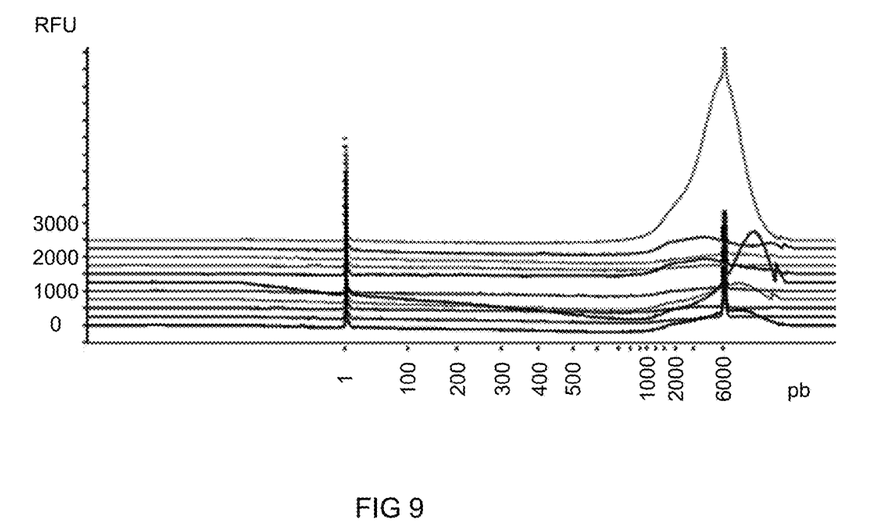

The same sonication procedure as that described in example 1 was applied. The results after 13 sonication cycles are shown in FIG. 9. A virtually total lack of fragmentation may be noted.

In a second comparative example, the other 16 microtubes were introduced into the holes of the support plate and suspended in the Bioruptor® Pico so as to position the microtubes at a depth D of 7.3 mm using the first rod for the support.

Figure 10:
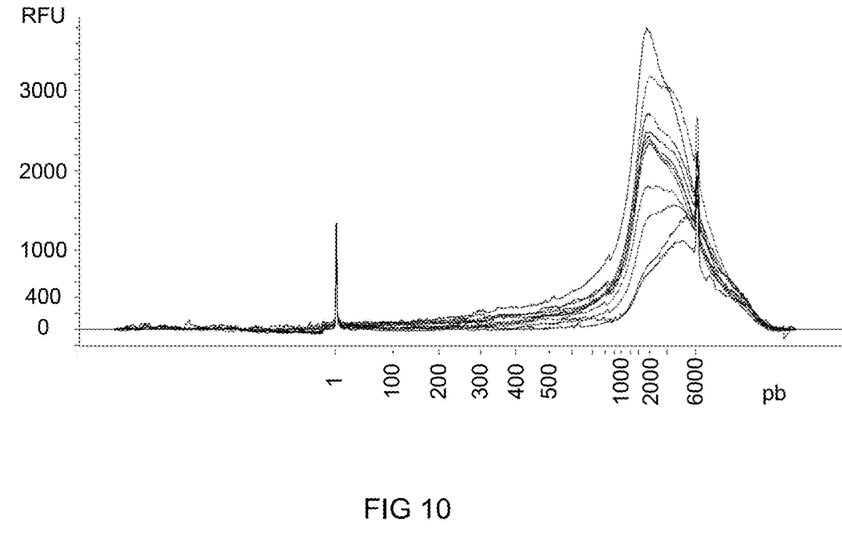

The same sonication procedure as that described in example 1 was applied. The results after 13 sonication cycles are shown in FIG. 10. It may be noted that fragments of a much larger size (approximately 2000 bp) were obtained.

It is therefore possible to deduce from the above examples that suspension at a depth D of 10.3 mm gives extraordinarily better results than suspension at 7.3 or 13 mm.

EXAMPLE 2

Influence of the Dimensions of the Support Plate of the Sample Tubes

The sonication samples were obtained according to the process of example 1. These samples were fragmented using support plates of different dimensions. The characteristic elements of these plates are the number of holes for introducing microtubes and the distance R, for arranging the microtubes, from the center of the plate. In each plate, introduction holes are formed over a circle of radius R with uniform spacing.

The same sonication procedure as that described in example 1 was applied. The microtubes were submerged to a depth D of 10.0 mm. The results are reported in table 1.

TABLE 1 results of the tests of example 2
(bp = base pairs; CV = coefficient of variance)

| Plate no. | # holes | R (mm) | # holes/R | Mean size (bp) | CV (%) |
|---|---|---|---|---|---|
| 1 | 16 | 30 | 0.53 | 213 | 9 |
| 2 | 18 | 30 | 0.60 | 265 | 15 |
| 3 | 20 | 30 | 0.67 | 281 | 16 |
| 4 | 22 | 30 | 0.73 | 451 | 35 |
| 5 | 24 | 35 | 0.69 | 371 | 20 |

EXAMPLE 3

Results from Several Different Sonication Devices

The sonication samples were obtained according to the process of example 1. The microtubes were suspended using the plate from example 1 (16 microtubes arranged around a circle of radius 30 mm), at a depth of submersion of 10.3 mm.

Two sonication devices were tested:

A1: Bioruptor® Pico (Diagenode, Belgium), configured at a frequency of 36 kHz-43 kHz; and A2: Water bath sonicator KJ-1006 (Shenzhen Kejie Ultrasonic Technology Co., Ltd, China), designed to operate at a fixed frequency of 40 kHz.

In both cases, a sonication of 15 cycles (30 s active period/30 s inactive period) was applied to a bath of distilled water at 4° C. The DNA fragments obtained were analyzed by a Fragment Analyzer™ (Advanced Analytical Technologies, Inc.) and their mean size and coefficient of variance (CV) were calculated.

With the device A1, fragments of a mean size of 208 bp with CV=7% were obtained. With the device A2, fragments of a mean size of 212 bp with CV=4.2% were obtained. The results are therefore comparable, which indicates that the conclusions obtained above relating to the depth of submersion and the way in which the samples are suspended are independent of the type of waterbath sonicator.

EXAMPLE 4

Use of a Plate with a Larger Diameter

The sonication samples were obtained according to the process of example 1. Thirty two (32) microtubes were suspended using a plate provided with 32 holes formed around a circle of radius R of 45 mm (#holes/R=0.71 mm$^{-1}$), at a depth of submersion of 10.3 mm in the tank of the sonicator A2 of example 3. The same sonication procedure as that described in example 1 was applied. The DNA fragments obtained were analyzed by a Fragment Analyzer™ (Advanced Analytical Technologies, Inc.) and their mean size and coefficient of variance (CV) were calculated. The mean size of the fragments was 212 bp and the CV was 8%.

EXAMPLE 5

Sonication at 20 kHz

The sonication samples were obtained according to the process of example 1. The microtubes were suspended using the plate from example 1 (16 microtubes arranged around a circle of radius 30 mm), at a depth of submersion of 10.3 mm in a Bioruptor® Plus device operating at a frequency of 20 kHz. A sonication of 15 cycles (30 s active period/30 s inactive period) was applied to a bath of distilled water at 4° C. The DNA fragments obtained were analyzed by a Fragment Analyzer™ (Advanced Analytical Technologies, Inc.) and their mean size and coefficient of variance (CV) were calculated. Fragments of a mean size of 2959 bp with CV=25% were obtained. The mean size is significantly larger compared to sonication at 40 kHz (example 3) due to a much more effective sonication at 40 kHz. By increasing the number of cycles (the sonication time) fragments of a smaller size could be obtained.

What is claimed is:

1. An assembly kit, comprising a sonication device and a support for sample tubes;

wherein the sonication device comprises a tank having a cover and at least one ultrasound wave generator coupled to an outer face of the tank, the ultrasound wave generator being designed to generate ultrasound waves having a frequency of between 20 kHz and 80 kHz, and the tank comprising a level indicator of the level of a liquid in the tank;

wherein the support for sample tubes comprises:

a support plate in the shape of a disk, the support plate including several holes arranged around a circumference of a circle such that the support plate is configured to support several sample tubes of a size of 0.2 ml, the holes having dimensions corresponding to the sample tubes, a rod having a lower end and an upper end, the rod being secured to the support plate at the lower end, such that the rod is concentric with the circle around which the holes are arranged, and a suspension element supported by the cover and configured to suspend the rod in the tank; and wherein the rod has a length such that, in an assembly position, the sample tubes introduced into the support plate are positioned with their lower ends between 8 mm and 12 mm below the level indicator.

2. The kit as claimed in claim 1, comprising said sample tubes of a size of 0.2 ml.

3. The kit as claimed in claim 1, wherein in the assembly position, the sample tubes introduced into the support plate are positioned with their lower end in a range between 9 mm and 11.5 mm below the level indicator.

4. The kit as claimed in claim 1, wherein the sample tubes comprise a flange which holds the sample tubes.

5. The kit as claimed in claim 1, wherein the support comprises a clamping means designed to clamp upper ends of the sample tubes onto the support plate.

6. The kit as claimed in claim 1, wherein the support plate is designed to support between 12 and 36 sample tubes of a size of 0.2 ml in a uniformly spaced arrangement around the circumference of the circle, the circle having a diameter between 50 mm and 100 mm.

7. The kit as claimed in claim 1, wherein the support plate is designed to support several sample tubes of a size of 0.2 ml in a uniformly spaced arrangement around the circumference of a circle, wherein a ratio between the number of sample tubes which the support plate allows to be supported and a radius of the circle is equal to or less than 0.7.

8. The kit as claimed in claim 1, wherein the suspension element is coupled to the support plate by the rod.

9. The kit as claimed in claim 8, wherein the suspension element comprises a plate formed on a cover of the tank.

10. The kit as claimed in claim 9, wherein the plate of the suspension element consists of a gear wheel designed to cause the support to turn about an axis of the rod, and the device comprises an actuator configured to actuate the gear wheel.

11. The kit as claimed in claim 1, wherein the ultrasound wave generator is designed to generate ultrasound waves having a frequency of between 28 kHz and 80 kHz.

12. A support for sample tubes of a size of 0.2 ml, comprising:

a support plate in the shape of a disk and comprising several holes arranged around a circumference of a circle such that the support plate is configured to support several sample tubes of a size of 0.2 ml, the holes having dimensions corresponding to the sample tubes;

a rod having a lower end and an upper end, the rod being secured to the support plate at the lower end, such that the rod is concentric with the circle around which the holes are arranged; and a suspension element configured to suspend the rod in a tank of a sonication device, the suspension element being supported by a cover of the tank, the tank comprising a level indicator of a level of liquid in the tank;

wherein the rod has a length such that, in an assembly position, the sample tubes introduced into the support plate are positioned with their lower ends between 8 mm and 12 mm below the level indicator of the level of liquid.

* * * * *